United States Patent [19]

Katsuyama et al.

[11] 3,944,556

[45] Mar. 16, 1976

[54] SPIRO-PYRAZOLINE DERIVATIVES AND METHOD FOR THE PRODUCTION THEREOF

[75] Inventors: Harumi Katsuyama; Hisatake Ono, Asaka, Japan

[73] Assignee: Fuji Photo Film Co., Ltd., Ashigara, Japan

[22] Filed: June 12, 1974

[21] Appl. No.: 478,498

Related U.S. Application Data

[62] Division of Ser. No. 276,998, Aug. 1, 1972, Pat. No. 3,859,303.

[30] Foreign Application Priority Data

Aug. 9, 1971 Japan .................................. 46-60061

[52] U.S. Cl.... 260/288 CE; 260/283 R; 260/286 R; 260/310 C

[51] Int. Cl.² .......................................... C07D 215/38

[58] Field of Search ............................... 260/288 CE

*Primary Examiner*—Nicholas S. Rizzo
*Assistant Examiner*—Mary C. Vaughn
*Attorney, Agent, or Firm*—Sughrue, Rothwell, Mion, Zinn & Macpeak

[57] ABSTRACT

Spiro-pyrazoline derivatives of the general formula

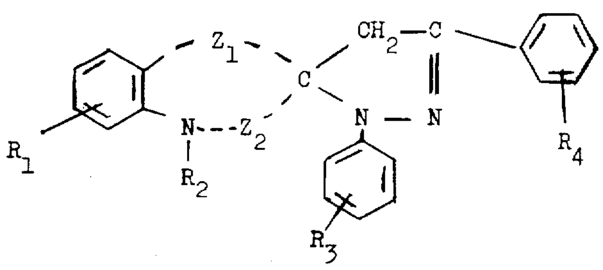

where $Z_1$, $Z_2$, $R_1$ to $R_4$ are as defined hereinafter and methods for their preparation are disclosed. The compounds are useful as organic photoconductors, organic fluorescent materials and as additives for silver salt and non-silver salt photographic materials.

4 Claims, No Drawings

SPIRO-PYRAZOLINE DERIVATIVES AND METHOD FOR THE PRODUCTION THEREOF

This is a division of application Ser. No. 276,998, filed Aug. 1, 1972, now U.S. Pat. No. 3,859,303.

BACKGROUND OF THE INVENTION

1. Field of the Invention

The present invention relates to spiro-pyrazoline derivatives having a novel skeleton and to a method for producing these spiro-pyrazoline derivatives having a novel skeleton.

More specifically, the invention is concerned with derivatives of spiro-pyrazoline, such as spiro(indoline-2,5′-pyrazoline), spiro(dihydroquinoline-2,5′-pyrazoline), spiro(dihydroquinoline-4,5′-pyrazoline), etc., and a method for their production comprising reacting a 2-methyleneindoline derivative, a 2-methylenedihydroquinoline derivative, 4-methylenedihydroquinoline derivative or a precursor thereof, such as a 2-methylindolenium salt derivative, a 2-methylquinolinium salt derivative, and 4-methylquinolinium salt derivative and benzphenylhydrazide chloride derivative in a solvent in the presence of an excessive amount of a base.

2. Description of the Prior Art

It is known that a hydrazide chloride gives an active intermediate product "nitrile imine" in the presence of a tertiary amine and a 1,3-dipole cycloaddition reaction with various multi-bonds takes place with this active material, as described, e.g., R. Huisgen, *Angewandte Chemie*, 75, 604(1963). However, it has never been reported that a spiro bond, as is obtained in this invention described hereinafter, is formed by the reaction of such a "nitrile imine" and an exo-methylene compound. Also, as the result of detailed research it has been confirmed that every exo-methylene compound does not always react under the conditions of the production method of this invention. Accordingly, it has become clear that only certain exo-methylene compounds can form spiro bonds similar to those in this invention. For instance, it is reported that when the active "nitrile imine" is allowed to stand in an inert solvent, a dimerized dihydrotetrazine is obtained. However, when the nitrile imine is reacted in the presence of 3-ethyl-2-methylenebenzthiazoline under the reaction conditions of this invention, no addition compound (1 : 1) having a spiro bond is obtained and only a dimer is isolated.

An object of the present invention is to provide spiro-pyrazoline derivatives having a novel structure, which can be used as organic photoconductive materials for electrophotography, organic fluorescent materials, and additives for silver salt and non-silver salt photographic materials and methods for preparing these derivatives.

SUMMARY OF THE INVENTION

The spiro-pyrazoline derivatives of this invention have the following general formula

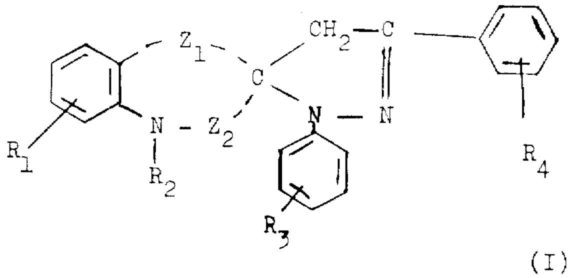

(I)

wherein $Z_1$ represents

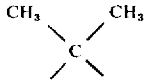

or —CH=CH—$_n$, in which $n$ is 0 or 1; $Z_2$ is —CH=CH—$_{1-n}$ when $Z_1$ is —CH=CH—$_n$ and $Z_2$ is absent when $Z_1$ is

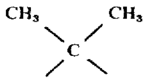

(i.e., giving rise to a C—N bond); $R_1$ represents a hydrogen atom, a halogen atom, a nitro group, a lower alkyl group having 1 to 3 carbon atoms, a lower alkoxyl group having 1 to 3 carbon atoms, or a lower alkoxycarbonyl group having 1 to 3 carbon atoms; $R_2$ represents a lower alkyl group having 1 to 3 carbon atoms, and $R_3$ and $R_4$ each represents a hydrogen atom, a halogen atom or a nitro group.

The method of preparing the spiro-pyrazoline derivatives of this invention can be generally represented by the following general reaction scheme (1).

Reaction Scheme (1):

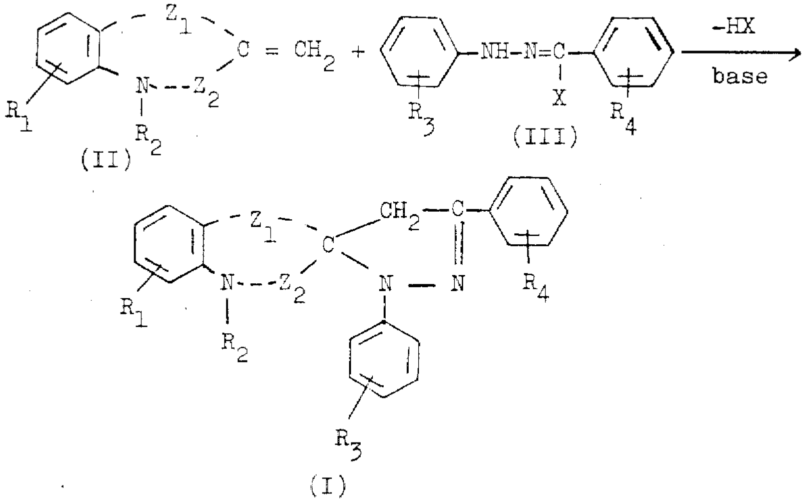

(II) (III)

(I)

in which an exo-methylene heterocyclic compound conjugated with a nitrogen atom (II) is reacted with a benzphenylhydrazide halide derivative (III) or the general reaction scheme (2).

Reaction Scheme (2):

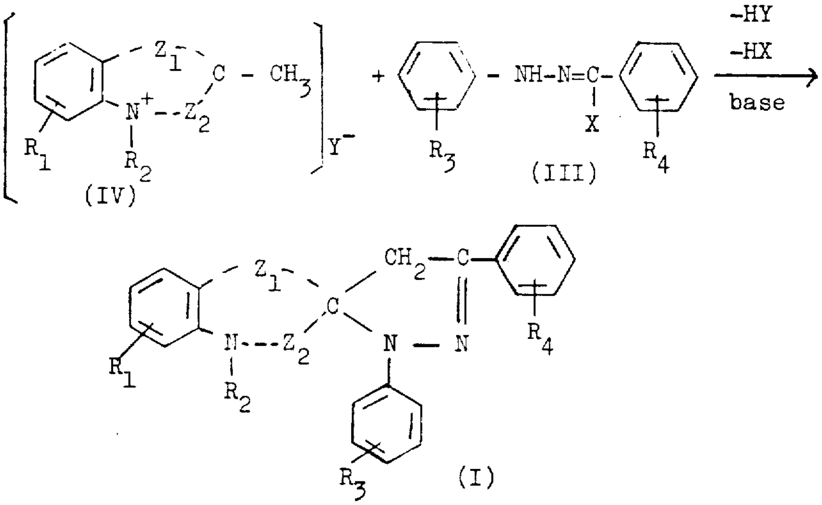

(IV) (III) (I)

in which a quaternary ammonium salt of an exo-methylene heterocyclic compound conjugated with a nitrogen atom (IV) is reacted with a benzphenylhydrazide halide derivative (III) wherein $Z_1$, $Z_2$, $n$, $R_1$, $R_2$, $R_3$ and $R_4$ in the above general reaction schemes (1) and (2) are as above defined and X represents a halogen atom and Y represents an acid residual group.

DETAILED DESCRIPTION OF THE INVENTION

As described above, the spiro-pyrazoline derivatives of this invention have the general formula (I). Suitable examples of halogen atoms are bromine, chlorine and iodine. Suitable examples of lower alkyl groups are methyl, ethyl, propyl and isopropyl groups. Suitable examples of lower alkoxy groups are methoxy, ethoxy, propoxy and isopropoxy groups and of lower alkoxycarbonyl groups are methoxycarbonyl and ethoxycarbonyl. Specific examples of acid residual groups are chlorine, bromine, iodine, p-tosylate or methyl sulfate.

Specific examples of the spiro-pyrazoline compounds of the general formula (I) are as follows.

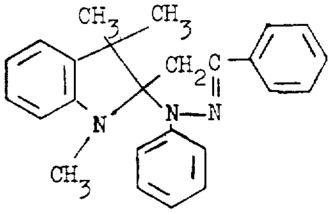

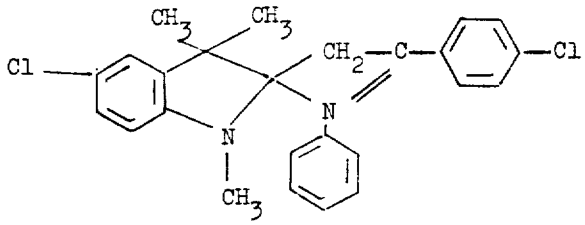

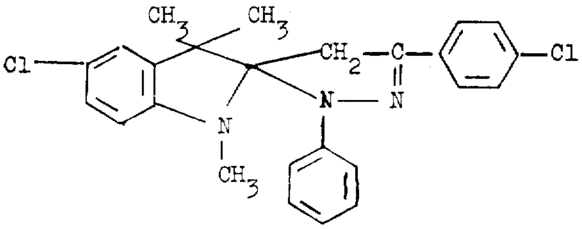

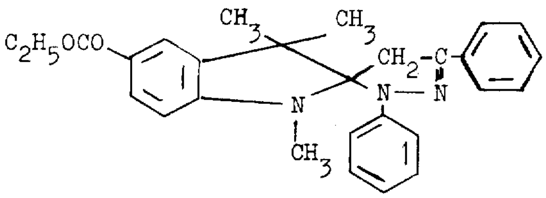

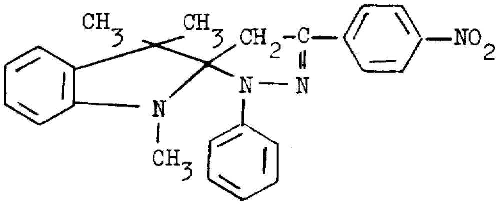

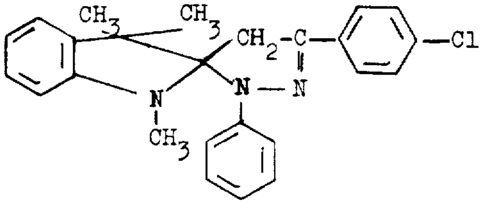

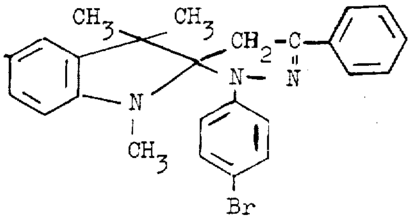

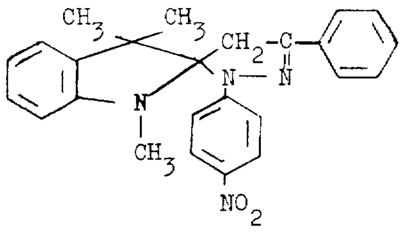

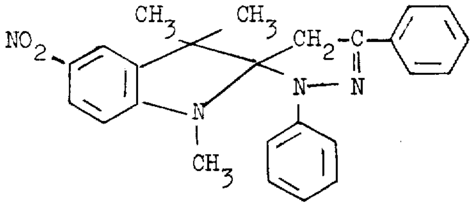

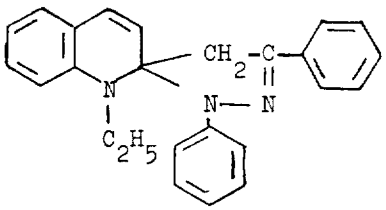

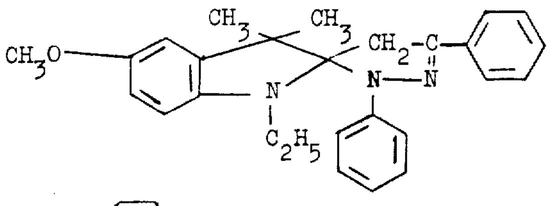

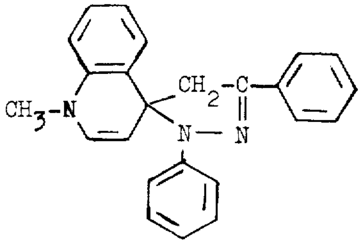

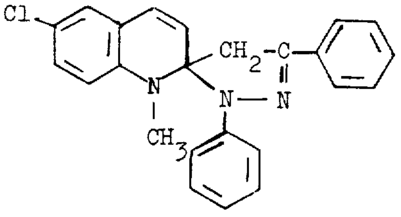

Examples of the exo-methylene heterocyclic compounds conjugated with a nitrogen atom (II), which can be used in the method of this invention, are 1-ethyl-2-methylene-1,2-dihydroquinoline, 1-ethyl-4-methylene-1,4-dihydroquinoline, 2-methylene-1,3,3-trimethylindoline, 3,3-dimethyl-1-ethyl-2-methyleneindoline, 5-chloro-2-methylene-1,3,3-trimethylindoline, 2-methylene-5-nitro-1,3,3-trimethylindoline, 5-ethoxycarbonyl-2-methylene-1,3,3-trimethylindoline, 2-methylene-1,3,3,5-tetramethylindoline, and the like.

Also, examples of the quaternary ammonium salt of the exo-methylene heterocyclic compound (IV) are 1,2-dimethylquinolimium-p-tosylate, 1,4-dimethylquinolinium-p-tosylate, 1,2,3,3-tetramethylindolenium-p-tosylate, 1-ethyl-2,3,3-trimethylindolenium iodide, 1-ethyl-2,3,3,5-tetramethylindolenium iodide, 5-ethoxycarbonyl-1,2,3,3-tetramethylindolenium-p-tosylate, 1-ethyl-5-methoxy-2,3,3-trimethylindolenium iodide, 5-nitro-1-propyl-2,3,3-trimethylindolenium bromide, 1,2-dimethylquinolinium-p-tosylate, and 6-chloro-1,2 -dimethylquinolinium-p-tosylate.

These exo-methylene heterocyclic compounds and the quaternary ammonium salts thereof are well known in the art as starting materials for the preparation of photographic sensitizing dyes and the exo-methylene heterocyclic compounds can be prepared by reacting the corresponding heterocyclic quaternary ammonium salt as a precursor with an acid-residue. The quaternary ammonium salt, for example, 1,3,3-trimethyl-2-methyleneindoline known as a Fischer's base, can be obtained by reacting 2,3,3-trimethylindoline with an alkylating agent such as methyl iodide, methyl p-tosylate, dimethyl sulfate or the like to produce a 1,2,3,3-tetramethyl indolenium salt which is then reacted with an acid residue.

The above exo-methylene heterocyclic compounds are active substances and generally unstable in air. For example, the indoline-type exo-methylene heterocyclic compounds usually turn into red-colored substances, and the quinoline-type exo-methylene heterocyclic compounds turn into red to black colored substances or resinous materials (See, *Chemistry*, Vol. 8, pp 505–513 (1953) published by the Riko Shuppan K.K., Japan).

The examples of benzphenylhydrazide halide derivative (III) are benzphenylhydrazide chloride, p-chlorobenz-phenylhydrazide chloride, p-nitrobenz-phenylhydrazide chloride, benz-p-chlorophenylhydrazide chloride, benz-p-nitrophenylhydrazide chloride, and phenyl-p-bromohydrazide chloride. These benzphenylhydrazide halide derivatives can be prepared from the corresponding benzphenylhydrazide derivatives by halogenation in accordance with the well-known methods such as those described in R. Huisgen et al., *Tetrahedron*, Vol. 17, pp 3–29 (1962). For example, benzphenylhydrazide chloride can be prepared by chlorinating benzphenylhydrazide with phosphorus pentachloride.

The spiro-pyrazoline derivative of this invention (I) can be produced by dissolving a mixture of the exo-methylene compound (II) as referred above or the quaternary salt thereof (IV) and a benzphenylhydrazide chloride derivative (III) in the solvents shown below and adding thereto a base to cause the reaction.

The molar ratio of the exo-methylene compound (II) or the quaternary ammonium salt thereof (IV) to the benzphenylhydrazide halide derivative (III) can range from 10 to 0.1, preferably, from 2 to 0.2. The amount of base somewhat varies depending upon the type of the reaction, i.e., the reaction schemes (1) and (2) previously described. In the reaction scheme (1) where the starting material is an exo-methylene compound (II) the base can be used in an amount of from 1 to 20 moles, preferably from 2 to 10 moles, per 1 mole of the compound (II).

In the reaction scheme (2) where the starting material is a quaternary ammonium salt (IV), the base can be used in an amount of from 2 to 25 moles, preferably from 2 to 15 moles, per 1 mole of the compound (II). The molar concentration of each of the reactants (III) and (II) or (IV) in the reaction mixture can range from 10 to 0.01 moles, preferably from 1 to 0.1 moles.

Suitable solvents which can be used in the above reaction are alcohols such as: ethers such as ethyl ether, dioxane, tetrahydrofuran, etc.; halogenated paraffins such as methylene chloride, chloroform, carbon tetracloride, ethylene chloride, trichloroethane, perchloroethane, tetrachloroethane, etc.; paraffins such as n-hexane, cyclohexane, heptane, etc.; benzene; toluene; and xylene.

Suitable examples of bases which can be used in the above described reaction are tertiary amines, secondary amines, or aromatic amines, such as triethylamine, tributylamine, piperidine, morpholine, pyridine, and the like and alkali metal hydroxides or salts such as sodium hydroxide, potassium hydroxide, sodium carbonate, potassium carbonate, sodium acetate, etc.

Because it has been found that the compound in this invention isomerizes under high temperature and acid conditions, the production of the compound in this invention must be so conducted that high temperature conditions are not employed and basic conditions are maintained during the reaction.

The base used in the above reaction serves as a scavenger for the hydrogen ion ($H^+$) contained as an impurity in the reactants and the solvent, which appears to increase the isomerization of the desired product. Since the concentration of the hydrogen ion in the reaction mixture is very low, the base may be used in a small amount and the basicity of the reaction mixture is not critical in the process of this invention.

Consequently, in the production of the compound of this invention, it is necessary to maintain the reaction temperature at from 0° to 150°C., preferably at temperatures of from room temperature (about 20° to 30°C) to about 100°C.

The reaction period generally required ranges from a few hours to about 48 hours but when the reaction temperature is about 80°C., the reaction period generally is from 30 minutes to about 1 hour.

After the reaction is completed, the salts are filtered away and the filtrate is concentrated, whereby crystals are obtained. The crystals are purified by recrystallizing from an appropriate solvent containing a small amount of an amine, for example, in an amount of from 0.01% to 5%, preferably from 0.1% to 1% by weight.

The solvent which can be used for the recrystallization includes alcohols such as methanol, ethanol or the like; ketones such as acetone, methylethyl ketone or the like; aromatic hydrocarbons such as toluene, benzene or the like; ethers such as tetrahydrofuran, dioxane or the like; alkyl acetates such as methyl acetate, ethyl acetate or the like; and a mixture thereof.

Although any amine may be used so long as it is soluble in the recrystallization solvent, the preferred amines are those bases previously enumerated for the reaction between the compound (II) or (IV) and the compound (III), particularly, tertiary and secondary amines.

In addition, it has been confirmed that where a compound which is unstable in air, such as methylenedihydroquinoline, is used as the starting material, a compound having less color is obtained without reducing the stability by conducting the reaction in an inert atmosphere such as an atmosphere of helium, hydrogen, nitrogen, argon, carbon dioxide gas or the like, preferably, nitrogen, argon or helium gas.

The production of the spiro-pyrazoline derivatives (I) of this invention will be described in detail hereinafter.

Because the spiro-pyrazoline derivatives prepared by the process of this invention have not yet been reported in the literature, the compounds were confirmed using the results obtained from elementary analysis, infrared absorption spectra, ultraviolet absorption spectra, nuclear magentic resonance spectra, mass spectrum analysis, etc.

For instance, the compound prepared by the method of this invention from 2-methine-1,3,3-trimethylindoline and p-nitro-benzphenylhydrazide chloride will be described below.

The elementary analysis of the compound prepared is as shown in the following table and these results are also confirmed by the results of a mass spectrum analysis.

| Elementary Analysis | Calculated (%) | Found (%) |
|---|---|---|
| C | 72.79 | 72.76 |
| H | 5.87 | 5.89 |
| N | 13.58 | 13.46 |

In the infrared absorption spectra of the compound, nitro group absorption was found at 1555 $cm^{-1}$ and 1335 $cm^{-1}$ but absorption belonging to the $\nu_{NH}$ group was not found.

In the nuclear magnetic resonance spectra of the compound, singlet peak of 3H was found at 1.22 ppm and 1.12 ppm, respectively.

This shows that the adjacent methyl groups at the 3-position of the indoline are not stereochemically equivalent and from this, it is concluded that the 2-position of the indoline is an asymetric carbon atom of $sp^3$ type, i.e., form a spiro bond.

Further, in the nuclear magnetic resonance spectrum the presence of a methyl group bonded to nitrogen was found at 2.23, a methylene group of the AB type at 3.28, and multiplet 13 nucleus protons at 6.0–8.1.

The resonance peaks of the AB type is a methylene group at the 4-position of pyrazoline ring and the bonding constant (J) was 18.0 c.p.s.

In the ultraviolet absorption spectra and visible absorption spectra of the compound in methanol, the absorption maximums were found at 260 mμ, 300 mμ (shoulder), and 435 mμ, which coincide with the absorption maximums of indoline and 3-(p-nitrophenyl)-1-phenylpyrazoline-2.

From the above analyses, it has been confirmed that the compound is 3'-(p-nitrophenyl)-1'-phenyl-1,3,3-trimethylspiro-(indoline-2,5'-pyrazoline-2) having a novel spiro structure.

Then the method of this invention will be explained in greater detail by referring to the following various examples.

EXAMPLE 1

1.7 g of 2-methylene-1,3,3-trimethylindoline and 2.3 g of benzphenylhydrazide chloride were dissolved in 50 ml of benzene and after adding 2 g of triethylamine to the solution, the mixture was stirred at room temperature. After 3 hours the triethylamine hydrochloride formed was filtered away and the fluorescent filtrate was concentrated under a reduced pressure and the oily residue was crystallized from ethanol, whereby 500 mg of colorless crystals of 1',3'-diphenyl-1,3,3-triethyl-spiro(indoline-2,5'-pyrazoline-2) was obtained. The yield for the product was 14%.

On the other hand, when the reaction was conducted for 6 hours at room temperature, the yield for the product was 44% and when the reaction mixture was heated for 30 minutes under refluxing, the same compound as above was obtained in a yield of 62%.

The compounds can be recrystallized from a mixture of ethanol and acetone but the solvent for the recrystallization must contain a few drops of a base such as triethylamine. That is to say, if a base is not present, the compound will isomerize.

The melting point of the compound was 125°-126°C and on melting an isomerized product was newly crystallized at the same time.

| | Elementary Analysis Calculated (%) | Found (%) |
|---|---|---|
| C | 81.71 | 82.00 |
| H | 6.86 | 7.02 |
| N | 11.44 | 11.53 |

In the infrared absorption spectra of the compound, a slight absorption based on the carbon-carbon double bond of pyrazoline was found at 1550 $cm^{-1}$.

EXAMPLE 2

2.1 g of 5-chloro-2-methylene-1,3,3-trimethylindoline and 2.3 g of benz-phenylhydrazide chloride were dissolved in 50 ml of benzene and after adding 2 g of triethylamine to the solution, the mixture was refluxed for 30 minutes. Then, by filtering away the triethylamine hydrochloride thus formed and treating the filtrate in the same way as described in Example 1, 2.2 g (53%) of crystals of 5-chloro-1',3'-diphenyl-1,3,3-trimethyl-spiro(indoline-3,5'-pyrazoline-2) having a melting point of 154°-155°C was obtained.

| | Elementary Analysis Calculated (%) | Found (%) |
|---|---|---|
| C | 74.70 | 74.55 |
| H | 6.01 | 6.05 |
| N | 10.45 | 10.42 |

EXAMPLE 3

2.1 g of 5-chloro-2-methylene-1,3,3-trimethylindoline and 2.7 g of p-chlorobenz-phenylhydrazide chloride were dissolved in benzene and after adding to the solution 2 g of triethylamine, the mixture was allowed to stand for 20 hours at room temperature. Thereafter, by treating the reaction product in the same way as described in Example 1, 2.2 g (52%) of 5-chloro-3'-(p-chlorophenyl)-1'-phenyl-1,3,3-trimethylspiro(indoline-2,5'-pyrazoline-2) was obtained. The melting point of the compound was 185°-186°C and the results of the elementary analysis of the compound are as shown in the following table.

| | Elementary Analysis Calculated (%) | Found (%) |
|---|---|---|
| C | 69.35 | 69.26 |
| H | 4.72 | 4.65 |
| N | 9.67 | 9.73 |

In the nuclear magnetic resonance spectra of the compound, a singlet of 3H was found at 0.98, 1.13, and 2.11 ppm using TMS internal standard in deuterated benzene; a quartet of 2H of the AB type was observed at 2.82 and 3.18; a bonding constant J = 18.6 cps.; and multiplet of 12H was found at 5.6-7.6.

EXAMPLE 4

2.45 g of 5-ethoxycarbonyl-2-methylene-1,3,3-trimethylindoline and 2.3 g of benz-phenylhydrazide chloride were reacted and then treated in the same way as described in Example 3 to obtain 2.8 g (65%) of 5-ethoxycarbonyl-1',3'-diphenyl-1,3,3-trimethylspiro-(indoline-2.5'-pyrazoline-2).

Also, when the same reaction was carried out for 1 hour at 55°C, the same compound as above was obtained in a yield of 63%.

| | Elementary Analysis Calculated (%) | Found (%) |
|---|---|---|
| C | 76.51 | 76.48 |
| H | 6.65 | 6.70 |
| N | 9.56 | 9.53 |

The nuclear magnetic resonance spectra (deuterated benzene, TMS internal standard) was: δ value (p.p.m.): 1.03, 1.21, and 2.14 (each 3H, singlet), 2.99 and 3.36 (2H, bonding constant J = 18.9 cps, AB type quartet), 4.29 (2H, J = 7.2 cps, triplet), 4.29 (2H, J = 7.2 cps, quartet), 5.8-7.3 (13H, multiplet).

EXAMPLE 5

1.73 g of methylene-1,3,3-trimethylindoline was reacted with 2.75 g of p-nitrobenz-phenylhydrazide chloride in the same way as described in Example 3. The triethylamine hydrochloride thus formed was filtered off and the filtrate was concentrated to give a red-brown oily material. The concentrate was subjected to a silica gel column chromatography using Wako Gel C-200 (trade name of silica gel made by Wako Junyaju K.K.) and the product was developed by n-hexane. The n-hexane effluent was concentrated to give 800 mg (20%) of a fluorescent red-orange compound. By the results from the various analyses as previously indicated, the compound obtained was confirmed to be 3'-(p-nitrophenyl)-1'-phenyl-1,3,3-trimethylspiro(indoline-2,5'-pyrazoline-2). The melting point of the compound was 160°-162°C.

| | Elementary Analysis Calculated (%) | Found (%) |
|---|---|---|
| C | 72.79 | 72.76 |
| H | 5.87 | 5.89 |
| N | 13.58 | 13.46 |

Furthermore, when the reaction period of time was extended further to 2 days, the yield of the product increased to 44%.

EXAMPLE 6

When 1.73 g of 2-methylene-1,3,3-trimethylindoline and 2.65 g of p-chlorobenz-phenylhydrazide chloride was treated in the same way as described in Example 3, 2.25 g (52%) of 3'-(p-chlorophenyl)-1'-phenyl-1,3,3-trimethylspiro(indoline-2,5'-pyrazoline-2) was obtained. The melting point of the product was 166°–168°C.

| | Elementary Analysis Calculated (%) | Found (%) |
|---|---|---|
| C | 74.70 | 74.74 |
| H | 6.01 | 6.00 |
| N | 10.45 | 10.46 |

EXAMPLE 7

1.87 g of 2-methylene-1,3,3,5-tetramethylindoline was reacted with 3.10 g of benz-(p-bromophenyl)hydrazide chloride in the same way as described in Example 3 to give 2.4 g (52%) of (p-bromophenyl)-3'-phenyl-1,3,3,5-tetramethylspiro-(indoline-2,5'-pyrazoline-2). The melting point of the product was 175°–176°C.

| | Elementary Analysis Calculated (%) | Found (%) |
|---|---|---|
| C | 69.32 | 69.30 |
| H | 5.35 | 5.28 |
| N | 8.68 | 8.59 |

EXAMPLE 8

1.73 g of 2-methylene-1,3,3-trimethylindoline and 2.75 g of benz-(p-nitrophenyl)hydrazide chloride were dissolved in 50 ml of ethyl ether and after adding to the solution 2 g of triethylamine, the mixture was stirred for 2 days at room temperature. When the crystals thus formed was recovered by filtration and washed with ethyl alcohol, the triethylamine hydrochloride produced as a by-product was dissolved away and 2.12 g of orange crystals were obtained. Furthermore, when the filtrate obtained in the above filtration step was concentrated under a reduced pressure and crystallized from ethyl alcohol, 0.65 g of the orange crystals of the same compound as above was also obtained.

By recrystallizing the compound obtained above from a solvent mixture of ethyl alcohol and tetrahydrofuran, 1'-(p-nitrophenyl)-3'-phenyl-1,3,3-trimethylspiro(indoline-2,5'-pyrazoline-2) having a melting point of 182°–183°C was obtained as columnar crystals.

| | Elementary Analysis Calculated (%) | Found (%) |
|---|---|---|
| C | 72.79 | 72.56 |
| H | 5.87 | 5.89 |
| N | 13.58 | 13.58 |

EXAMPLE 9

2.28 g of 2-methylene-5-nitro-1,3,3-trimethylindoline and 2.31 g of benz-phenylhydrazide chloride were dissolved in 50 ml of tetrahydrofuran and after adding to the solution 2 g of triethylamine, the mixture was stirred for 2 days at room temperature. After filtering away the triethylamine hydrochloride formed in the reaction, the filtrate was concentrated under a reduced pressure. Then, by crystallizing the oily material thus obtained from ethanol and removing the unreacted hydrazide chloride, 650 mg of the crystals of 1', 3'-diphenyl-5-nitro-1,3,3-trimethylspiro-(indoline-2,5'-pyrazoline-2) was obtained. The melting point of the product was 150°–151°C.

| | Elementary Analysis Calculated (%) | Found (%) |
|---|---|---|
| C | 72.79 | 72.65 |
| H | 5.87 | 5.85 |
| N | 13.58 | 13.47 |

EXAMPLE 10

3.80 g of 1-ethyl-5-methoxy-2,3,3-trimethylindolenium iodide was dissolved in a solvent mixture of 30 ml of benzene and 20 ml of ethanol under heating. After adding to the solution 4 g of triethylamine, the mixture was maintained at 50°C for about 30 minutes and then cooled to room temperature. Then, 2.65 g of p-chloro-benz-phenylhydrazide chloride was further added to the solution and the mixture was refluxed for 30 minutes. The salt thus precipitated was filtered away, the fluorescent filtrate was concentrated under a reduced pressure, and the remaining oily material was crystallized from ethanol, the crystals being recovered by filtration.

By recrystallizing the product obtained from a mixture of ethanol, a small amount of acetone and a few drops of triethylamine, 2.34 g of 3'-(p-chlorophenyl)-3,3-dimethyl-1-ethyl-5-methoxy-1'-phenylspiro(indoline-2,5'-pyrazoline-2) was obtained in a yield of 52%. The melting point of the product was 143°–145°C.

| | Elementary Analysis Calculated (%) | Found (%) |
|---|---|---|
| C | 73.44 | 73.47 |
| H | 5.54 | 5.55 |
| N | 7.22 | 7.25 |

EXAMPLE 11

1.72 g of 1-ethyl-2-methylene-1,2-dihydroquinoline and 2.33 g of benz-phenylhydrazide chloride were dissolved in benzene and after adding to the solution 2 g of triethylamine, the mixture was stirred for 5 hours at room temperature. By recovering the crystals thus formed by filtration and washing away the triethylamine hydrochloride from the crystals with ethanol, 2.60 g of 1',3'-diphenyl-1-ethyl-spiro(1,2-dihydroquinoline-2,5'-pyrazoline-2) was obtained in a yield of 70%. The product was purified by recrystallizing from ethanol. The melting point thereof was 109°–110°C.

| | Elementary Analysis Calculated (%) | Found (%) |
|---|---|---|
| C | 82.16 | 81.96 |
| H | 6.34 | 6.24 |
| N | 11.50 | 11.73 |

In the infrared absorption spectra of the product, the carbon-carbon double bond at the 3-position and 4-position of dihydroquinoline was found at 1640 $cm^{-1}$ and further the carbon-carbon double bond of pyrazoline was found at 1550 $cm^{-1}$ as a shoulder.

In the nuclear magnetic resonance spectra as the $\delta$ value (p.p.m.) of TMS internal standard in deutrerated benzene, the following absorptions were observed.

0.82 (3H, triplet, J = 7.2 cps), 2.94 (2H, quartet, J = 7.2 cps), 3.23, 2.75 (AB type 2H, quartet, J = 18.6 cps), 5.17 (1H, doublet, 31.6 cps), 6.24 (1H, doublet, 31.6 cps), 6.3–7.8 (14H, multiplet).

In addition, when the reaction was conducted in a nitrogen gas atmosphere, the same product as described above but less colored was obtained.

EXAMPLE 12

3.51 g of 1,4-dimethylquinolinium-p-tosylate was reacted with 2.33 g of benz-phenylhydrazide chloride in the same way as described in Example 10 to give 2.30 g of 1',3'-diphenyl-1-methylspiro(1H,-4H-dihydroquinoline-4,5'-pyrazoline-2) with a yield of 62%. The melting point of the product was 102°–103°C.

| | Elementary Analysis Calculated (%) | Found (%) |
|---|---|---|
| C | 82.02 | 82.27 |
| H | 6.02 | 5.92 |
| N | 11.95 | 11.89 |

EXAMPLE 13

4.00 g of 6-chloro-1,2-dimethylquinolinium-p-tosylate was reacted with 2.33 g of benz-phenylhydrazide chloride in the way as described in Example 10 to give 2.05 g (52%) of 6-chloro-1',3'-diphenyl-1-methylspiro(1,2-dihydroquinoline-2.5'-pyrazoline-2). The melting point of the product was 130°–132°C.

| | Elementary Analysis Calculated (%) | Found (%) |
|---|---|---|
| C | 74.73 | 74.70 |
| H | 5.19 | 5.21 |
| N | 10.90 | 10.95 |

While the invention has been described in detail and with reference to specific embodiments thereof, it is apparent that various changes and modifications can be made therein without departing from the spirit and scope thereof.

What is claimed is:

1. A spiro-pyrazoline compound having the formula (I)

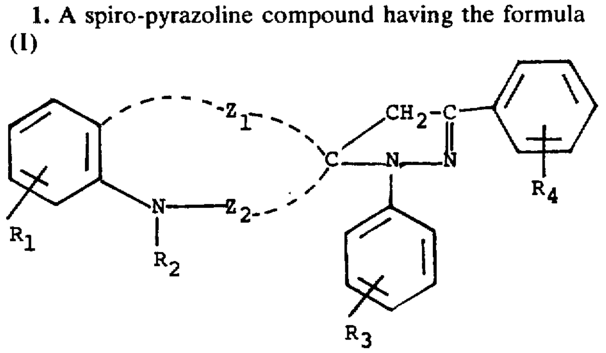

wherein $Z_1$ represents $-CH{=}CH-_n$ in which $n$ is 0 or 1; $Z_2$ is $-CH{=}CH-_{1-n}$ ; $R_1$ represents hydrogen, halogen, nitro, lower alkyl having from 1 to 3 carbon atoms, lower alkoxyl of from 1 to 3 carbon atoms or lower alkoxycarbonyl wherein the alkoxy group has from 1 to 3 carbon atoms; $R_2$ represents lower alkyl having from 1 to 3 carbon atoms; and $R_3$ and $R_4$ each represents hydrogen, halogen, or nitro.

2. The spiro-pyrazoline compound of claim 1 wherein said compound is

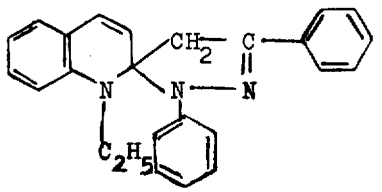

3. The spiro-pyrazoline compound of claim 1 wherein said compound is

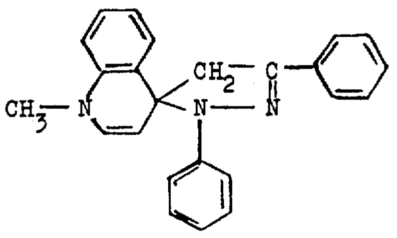

4. The spiro-pyrazoline compound of claim 1 wherein said compound is

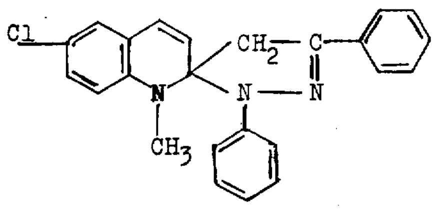

* * * * *